(12) United States Patent
Viscomi et al.

(10) Patent No.: US 7,045,620 B2
(45) Date of Patent: May 16, 2006

(54) POLYMORPHOUS FORMS OF RIFAXIMIN, PROCESSES FOR THEIR PRODUCTION AND USE THEREOF IN MEDICINAL PREPARATIONS

(75) Inventors: Giuseppe C. Viscomi, Bologna (IT); Manuela Campana, Bologna (IT); Dario Braga, Bologna (IT); Donatella Confortini, Bologna (IT); Vincenzo Cannata, Bologna (IT); Denis Severini, Bologna (IT); Paolo Righi, Bologna (IT); Goffredo Rosini, Bologna (IT)

(73) Assignee: Alfa Wassermann, S.p.A., Alanno (IT)

( * ) Notice: Subject to any disclaimer, the term of this patent is extended or adjusted under 35 U.S.C. 154(b) by 197 days.

(21) Appl. No.: 10/728,090

(22) Filed: Dec. 5, 2003

(65) Prior Publication Data
US 2005/0101598 A1  May 12, 2005

(30) Foreign Application Priority Data
Nov. 7, 2003  (IT)  .......................... MI2003A2144

(51) Int. Cl.
*C07D 498/22*  (2006.01)
(52) U.S. Cl. .................................... 540/456
(58) Field of Classification Search ................ 540/456; 514/393
See application file for complete search history.

(56) References Cited

U.S. PATENT DOCUMENTS 4,341,785 A * 7/1982 Marchi et al. .............. 514/338
4,557,866 A   12/1985 Cannata

FOREIGN PATENT DOCUMENTS

EP    0 161 534 A2   11/1985

* cited by examiner

*Primary Examiner*—Bruck Kifle
(74) *Attorney, Agent, or Firm*—Rothwell, Figg, Ernst & Manbeck, P.C.

(57) ABSTRACT

Crystalline polymorphous forms of the rifaximin (INN) antibiotic named rifaximin α and rifaximin β, and a poorly crystalline form named rifaximin γ have been discovered. These forms are useful in the production of medicinal preparations for oral and topical use and can be obtained by means of a crystallization process carried out by hot-dissolving the raw rifaximin in ethyl alcohol and by causing the crystallization of the product by the addition of water at a determinate temperature and for a determinate period of time. The crystallization is followed by drying carried out under controlled conditions until a specific water content is reached in the end product.

20 Claims, 3 Drawing Sheets

POLYMORPHOUS FORMS OF RIFAXIMIN, PROCESSES FOR THEIR PRODUCTION AND USE THEREOF IN MEDICINAL PREPARATIONS

BACKGROUND OF THE INVENTION

Rifaximin (INN; see The Merck Index, XIII Ed., 8304) is an antibiotic pertaining to the rifamycin class, specifically it is a pyrido-imidazo rifamycin which is described and claimed in the Italian Patent IT 1154655. European Patent EP 0161534 describes and claims a process for its production starting from rifamycin O (The Merck Index, XIII Ed., 8301).

Both of these patents describe the purification of rifaximin in a generic way stating that the crystallization can be carried out in suitable solvents or solvent systems and summarily showing in some examples that the product coming from the reaction can be crystallized from the 7:3 mixture of ethyl alcohol/water and can be dried both under atmospheric pressure and under vacuum. Neither of these patents disclose the experimental conditions of crystallization and drying, nor any distinctive crystallographic characteristic of the resulting product.

The presence of different polymorphs was previously unknown and therefore the experimental conditions described in both patents had been developed to produce a homogeneous product having a suitable purity from the chemical point of view, apart from the crystallographic aspects of the product itself.

It has now been found, unexpectedly, that some polymorphous forms exist whose formation, in addition to the solvent, depends on the conditions of time and temperature at which both the crystallization and the drying are carried out.

These orderly polymorphous forms are identified as rifaximin α (FIG. 1) and rifaximin β (FIG. 2) on the basis of their respective specific diffractograms, while the poorly crystalline form with a high content of amorphous component is be identified as rifaximin γ (FIG. 3) in the present application.

The polymorphous forms of rifaximin have been characterized using powder X-ray diffraction.

The identification and characterization of these polymorphous forms and, contemporarily, the definition of the experimental conditions for obtaining them is very important for a compound endowed with pharmacological activity which, like rifaximin, is marketed as a medicinal preparation both for human and veterinary use. It is known that the polymorphism of a compound that can be used as an active principle in a medicinal preparation can influence the pharmaco-toxicologic properties of the drug. Different polymorphous forms of an active principle can have different bioavailability, solubility, stability, colour, compressibility, flowability and workability with consequent modification of the profiles of toxicological safety, clinical effectiveness and productive efficiency.

The significance of different polymorphous forms is confirmed by the fact that the authorities which regulate the grant of authorization for the marketing of drugs require that the manufacturing methods of the active principles are standardized and controlled in such a way that they give homogeneous and sound results in terms of polymorphism of the production batches (CPMP/QWP/96, 2003—Note for Guidance on Chemistry of new Active Substance; CPMP/ICH/367/96—Note for guidance specifications: test procedures and acceptance criteria for new drug substances and new drug products: chemical substances; Date for coming into operation: May 2000).

The need for the above-mentioned standardization has been further strengthened, just in the field of rifamycin antibiotics, by Henwood S. Q., de Villiers M. M., Liebenberg W. and Lötter A. P., Drug Development and Industrial Pharmacy, 26 (4), 403–408, (2000), who have ascertained that different production batches of rifampicin (INN) made by different manufacturers show different polymorphous characteristics, and as a consequence they show different profiles of dissolution together with consequent alteration of the respective pharmacological properties.

By applying the processes of crystallization and drying generically disclosed in the previous patents IT 1154655 and EP 0161534 it has been found that under some experimental conditions the poorly crystalline form of rifaximin is obtained while under other experimental conditions the other crystalline polymorphous forms of rifaximin are obtained. Moreover it has been found that some parameters, which are not disclosed in the above-mentioned patents (e.g. the conditions of preservation and the relative humidity of the ambient) have a surprising effect on the form of the polymorph.

The polymorphous forms of rifaximin of the present patent application were not previously seen or hypothesized. The general thought at the time was that a sole homogeneous product would always be obtained regardless of which method was chosen within the range of the described conditions, irrespective of the conditions used for crystallizing, drying and preserving.

It has now been found that the formation of the α, β and γ forms depends on the presence of water within the crystallization solvent, on the temperature at which the product is crystallized and on the amount of water present into the product at the end of the drying phase.

The form α, the form β and the form γ of rifaximin have then been synthesised and they are the object of the present invention.

Moreover it has been found that the presence of water in rifaximin in the solid state is reversible, so that absorption and/or cession of water can take place under suitable ambient conditions. Consequently, rifaximin is susceptible to transition from one form to another, also remaining in the solid state, without the need to be dissolved and recrystallized. For example, the polymorph α, by adding water by hydration until a content higher than 4.5% is reached, turns into the polymorph β, which in its turn, loosing water by drying until a content lower than 4.5% is reached, turns into the polymorph α.

These results have a remarkable importance as they determine the conditions of industrial manufacturing of some steps which would previously not have been considered critical for the determination of the polymorphism of a product, like for instance the washing of a crystallized product, or the conditions of preservation of the end product, or the characteristics of the container in which the product is preserved.

The above-mentioned α, β and γ forms can be advantageously used as pure and homogeneous products in the manufacture of medicinal preparations containing rifaximin.

As previously indicated, the process for manufacturing rifaximin from rifamycin O disclosed and claimed in EP 0161534 is deficient from the point of view of the purification and identification of the product obtained. It shows some limits also from the synthetic point of view as regards, for instance, the very long reaction times, from 16 to 72 hours, which is unsuitable for industrial use and moreover because it does not provide for the in situ reduction of the oxidized rifaximin that may be formed within the reaction mixture.

Therefore, a further object of the present invention is an improved process for the industrial manufacturing of the α, β and γ forms of rifaximin, herein claimed as products and usable as defined and homogeneous active principles in the manufacture of the medicinal preparations containing such active principle.

DESCRIPTION OF THE INVENTION

As stated above, the form α, the form β and the form γ of the antibiotic known as rifaximin (INN), processes for their production and the use thereof in the manufacture of medicinal preparations for oral or topical administration, are the object of the present invention.

One embodiment of the present invention comprises reacting one molar equivalent of rifamycin O with an excess of 2-amino-4-methylpyridine, preferably from 2.0 to 3.5 molar equivalents, in a solvent mixture made of water and ethyl alcohol in volumetric ratios between 1:1 and 2:1, for a period of time between 2 and 8 hours at a temperature between 40° C. and 60° C.

At the end of the reaction the reaction mass is cooled to room temperature and is added with a solution of ascorbic acid in a mixture of water, ethyl alcohol and aqueous concentrated hydrochloric acid, under strong stirring, in order to reduce the small amount of oxidized rifaximin that forms during the reaction. Finally the pH is brought to about 2.0 by means of a further addition of a concentrated aqueous solution of hydrochloric acid, in order to better remove the excess of 2-amino-4-methylpyridine used in the reaction. The suspension is filtered and the obtained solid is washed with the same solvent mixture water/ethyl alcohol used in the reaction. Such semifinished product is called "raw rifaximin".

The raw rifaximin can be directly submitted to the subsequent step of purification. Alternatively, if the semifinished product is to be preserved for a long time, the raw rifaximin can be dried under vacuum at a temperature lower than 65° C. for a period of time between 6 and 24 hours, such semifinished product is called "dried raw rifaximin".

The so obtained raw rifaximin and/or dried raw rifaximin are purified by dissolving them in ethyl alcohol at a temperature between 45° C. and 65° C. and by crystallizing them by addition of water, preferably in weight amounts between 15% and 70% in respect of the amount by weight of the ethyl alcohol used for the dissolution, and by keeping the obtained suspension at a temperature between 50° C. and 0° C. under stirring during a period of time between 4 and 36 hours.

The suspension is filtered and the obtained solid is washed with water and dried under vacuum or under normal pressure, with or without a drying agent, at a temperature between room temperature and 105° C. for a period of time between 2 and 72 hours.

The achievement of the α, β and γ forms depends on the conditions chosen for the crystallization. In particular, the composition of the solvent mixture from which the crystallization is carried out, the temperature at which the reaction mixture is kept after the crystallization and the period of time at which that temperature is kept, have proven to be critical.

More precisely, the rifaximin γ is obtained when the solution is brought to a temperature between 28° C. and 32° C. in order to cause the beginning of precipitation and the obtained suspension is further cooled to 0° C. and kept at this temperature for a period of time between 6 and 24 hours.

The suspension is filtered, the solid is washed with demineralized water and is dried until a water content between 1.0% and 2.0% is reached.

The α and β rifaximins are obtained when the temperature is first brought to a value between 28° C. and 32° C. in order to cause the beginning of the crystallization, then the suspension is brought to a temperature between 40° C. and 50° C. and kept at this value for a period of time between 6 and 24 hours, then the suspension is quickly cooled to 0° C., in a period of time between 15 minutes and one hour, is filtered, the solid is washed with water and then dried.

The step of drying plays an important part in obtaining the α and β polymorphous forms of the rifaximin and has to be checked by means of a suitable method for determining the water content, like for instance the Karl Fisher method, in order to check the amount of remaining water present in the product after drying.

The production of rifaximin α or of rifaximin β during drying depends on the amount of water remaining at the end, higher or lower than 4.5%, and not from the experimental conditions of pressure and temperature at which this critical limit of water percentage is achieved. In fact, the two polymorphous forms, with higher or lower water content, can be obtained by drying under vacuum or at atmospheric pressure, at room temperature or at high temperatures, in the presence or in the absence of drying agents, provided that the drying is conducted for the amount of time necessary so that the water percent characteristic for each polymorphous form is achieved.

The polymorphous form β is obtained when the drying of the product, crystallized and washed with water, is stopped at values of water higher than 4.5%, as measured by means of the Karl Fisher method, preferably between 5.0% and 6.0%. The polymorphous form α is obtained by continuing the drying until values lower than 4.5%, preferably between 2.0% and 3.0% are reached. Both the form γ and the forms α and β of rifaximin are hygroscopic, they absorb water in a reversible way in the presence of suitable conditions of pressure and humidity in the ambient environment and are susceptible of transformation from one form to another.

The polymorphous form α, kept in an ambient environment with a relative humidity higher than 50% for a period of time between 12 and 48 hours, turns into the polymorphous form β, which in turn, by drying until an amount of water lower than 4.5% is reached, preferably comprised between 2.0% and 3.0%, turns into the polymorphous form α.

Another type of transition happens between the form γ and the forms α and β. It takes place dependent upon the temperatures kept during the precipitation of rifaximin.

In particular the form γ turns into the forms α or β by keeping a suspension of the form γ of the rifaximin in a solvent mixture of ethyl alcohol/water 7:3 (V/V) at a temperature between 38° C. and 50° C. with strong stirring for a prolonged period of time, preferably between 6 and 36 hours.

Filtration and washing with demineralized water, then drying until a content of water higher than 4.5% is reached, preferably between 5.0% and 6.0%, results in the polymorphous form β, while carrying on the drying until a content of water lower than 4.5% is reached, preferably between 2.0% and 3.0%, gives the form α.

The rifaximins α and β can turn into rifaximin γ by dissolving them in ethyl alcohol and then treating the resulting solution as previously described for the preparation of the form γ.

These transitions from one form to another are very important in the ambit of the present invention, because they can be an alternative manufacturing method for obtaining the form desired for the production of the medicinal preparations. Therefore, the process that allows the conversion of rifaximin γ into rifaximin α or β in a valid industrial manner, the process that allows the conversion of rifaximin α or β into rifaximin γ in a valid industrial manner, the process that allows the conversion of rifaximin α into rifaximin β in a valid industrial manner or rifaximin β into rifaximin α, are important parts of the present invention.

The process concerning the transformation of rifaximin γ into rifaximin α or rifaximin β comprises suspending rifaximin γ in a solvent mixture made of ethyl alcohol/water in the volumetric ratio 7:3, warming the suspension until a temperature between 38° C. and 50° C. is reached and keeping it at this temperature under strong stirring for a period of time between 6 and 36 hours. The suspension is then filtered, the solid is washed with water and dried resulting in the polymorphous form β when the drying is carried on until a water percent between 5.0% and 6.0% as measured with the Karl Fisher method is reached, and the polymorphous form α when the drying is continued until a water percent between 2.0% and 3.0% is reached.

The process for getting the form γ starting from rifaximin α or β comprises dissolving the α or β form in ethyl alcohol with stirring, at a temperature between 50° C. and 60° C., adding demineralized water until an ethyl alcohol/water volumetric ratio of 7:3 is reached, cooling the solution under strong stirring to 30° C., cooling the plentiful precipitate to 0° C. and keeping the suspension under stirring at 0° C. for a period of time between 6 and 24 hours. The suspension is then filtered, the solid is washed with water and dried until a water percent lower than 2.0% is reached, thereby obtaining rifaximin γ.

The process concerning the transformation of the form α into the form β consists of keeping the rifaximin α, in the powder form, in an ambient environment having a rate of relative humidity higher than 50% for a period of time necessary, generally between 12 and 48 hours, in order to get a water content in the powder higher than 4.5%.

The process concerning the transformation of the form β into the form α consists of submitting the powder of rifaximin β to a process of drying under vacuum or under conditions of normal pressure, with or without a drying agent, at a temperature between room temperature and 105° C., for a period of time between 2 and 72 hours, in order to get the water content in the powder lower than 4.5%, preferably between 2.0% and 3.0%.

From the above discussion, it is clear that during the phase of preservation of the product particular care has to be taken so that the ambient conditions do not change the water content of the product. This can be achieved by preserving the product in ambients having controlled humidity or in closed containers that do not allow a significant exchange of water with the exterior ambient environment.

The polymorph called rifaximin α is characterised by a water content lower than 4.5%, preferably between 2.0% and 3.0% and from a powder X-ray diffractogram (reported in FIG. 1) which shows peaks at the values of the diffraction angles 2θ of 6.6°; 7.4°; 7.9°; 8.8°; 10.5°; 11.1°; 11.8°; 12.9°; 17.6°; 18.5°; 19.7°; 21.0°; 21.4°; 22.1°. The polymorph called rifaximin β is characterized by a water content higher than 4.5%, preferably between 5.0% and 6.0%, and from a powder X-ray diffractogram (reported in FIG. 2) which shows peaks at the values of the diffraction angles 2θ of 5.4°; 6.4°; 7.0°; 7.8°; 9.0°; 10.4°; 13.1°; 14.4°; 17.1°; 17.9°; 18.3°; 20.9°.

The polymorph called rifaximin γ is characterized by a much poorer powder X-ray diffractogram because of the poor crystallinity; the significant peaks are at the values of the diffraction angles 2θ of 5.0°; 7.1°; 8.4° as reported in FIG. 3.

The diffractograms have been carried out by means of the Philips X'Pert instrument endowed with Bragg-Brentano geometry and under the following working conditions:
X-ray tube: Copper
Radiation used: K (α1), K (α2)
Tension and current of the generator: KV 40, mA 40
Monocromator: Graphite
Step size: 0.02
Time per step: 1.25 seconds
Starting and final angular 2θ value: 3.0°÷30.0°

The evaluation of the content of water present in the analyzed samples has always been carried out by means of the Karl Fisher method.

The forms α, β and γ can be advantageously used in the production of medicinal preparations having antibiotic activity, containing rifaximin, for both oral and topical use. The dosage is generally between 10 mg to 10 g, preferably 20 mg to 5 g per day per adult. If rifaximins α, β or γ are combined with other known antibiotics such as erythromycin, fluoroquinolones, vancomycin, tetraciclines, trimetoprim, fusidic acid, isoniazid, fosfomycin, clofazmin, dapsone, or aminoside, the dosage of rifaximin can be suitably adjusted.

The medicinal preparations for oral use contain rifaximin α or β or γ together with the usual excipients as diluting agents like mannitol, lactose and sorbitol; binding agents like starchs, gelatines, sugars, cellulose derivatives, natural gums and polyvinylpyrrolidone; lubricating agents like talc, stearates, hydrogenated vegetable oils, polyethylenglycol and colloidal silicon dioxide; disintegrating agents like starchs, celluloses, alginates, gums and reticulated polymers; coloring, flavoring and sweetening agents.

All the solid preparations administrable by oral route can be used in the ambit of the present invention, for instance coated and uncoated tablets, capsules made of soft and hard gelatin, sugar-coated pills, lozenges, wafer sheets, pellets and powders in sealed packets.

The medicinal preparations for topical use contain rifaximin α or β or γ together with the usual excipients like white petrolatum, white wax, lanolin and derivatives thereof, stearylic alcohol, propylenglycol, sodium lauryl sulfate, ethers of the fatty polyoxyethylene alcohols, esters of the fatty polyoxyethylene acids, sorbitan monostearate, glyceryl monostearate, propylene glycol monostearate, polyethylene glycols, methylcellulose, hydroxymethylpropylcellulose, sodium carboxymethylcellulose, colloidal aluminium and magnesium silicate, sodium alginate.

All the topical preparations can be used in the ambit of the present invention, for instance the ointments, the pomades, the creams, the gels and the lotions.

Figure 1:
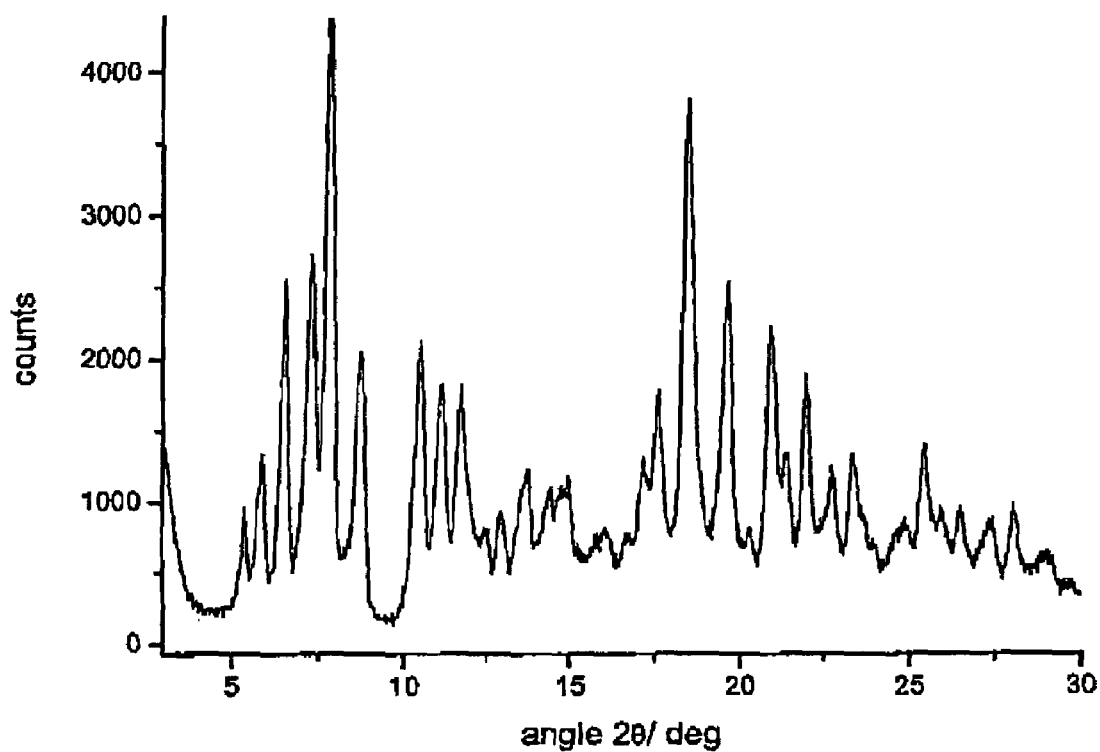
FIG. 1 shows a diffractogram of polymorph alpha.
Figure 2:
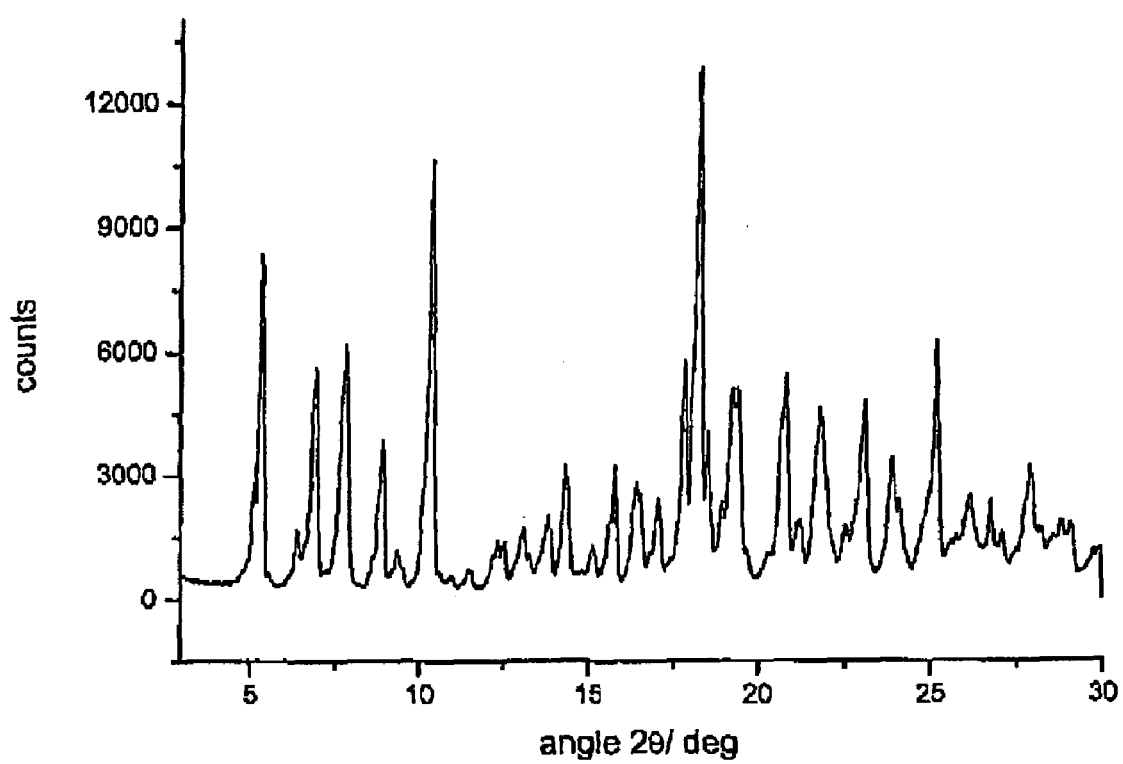
FIG. 2 shows a diffractogram of polymorph beta.
Figure 3:
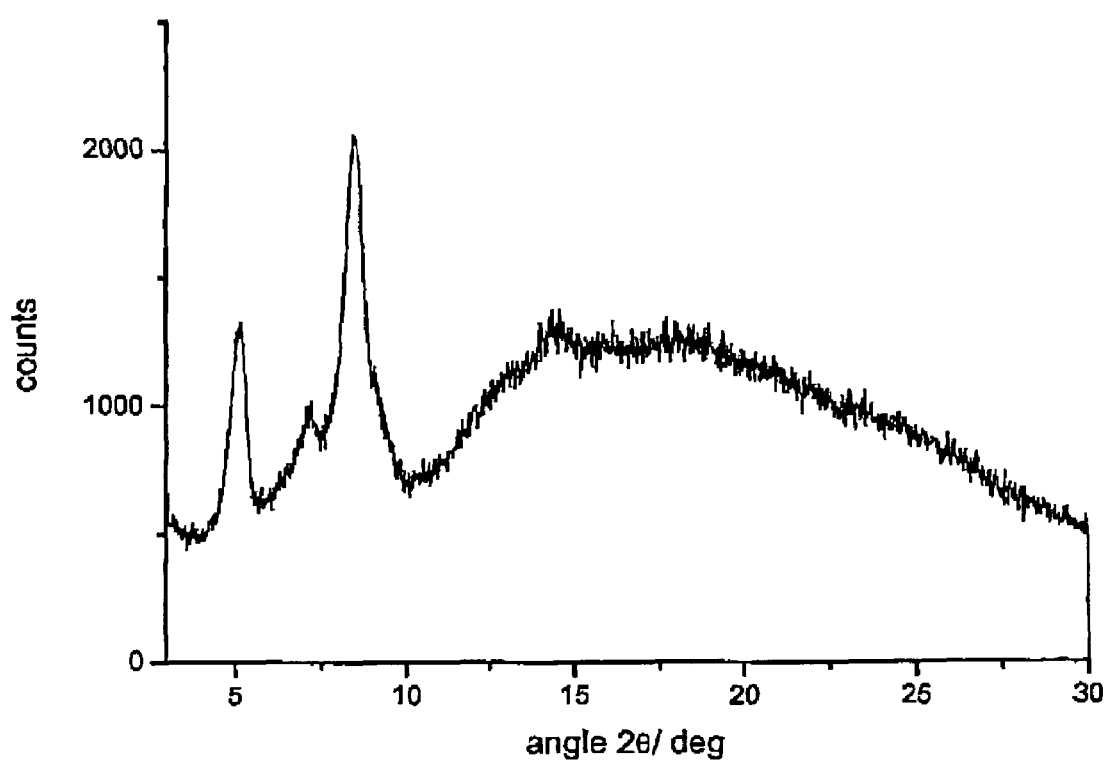
FIG. 3 shows a diffractogram of polymorph gamma.

The invention is hereinbelow illustrated by some examples which are not intended to limit the invention. The results show that the forms α, β and γ can be obtained by manipulating the above mentioned conditions of crystallization and drying.

EXAMPLE 1

Preparation of Raw Rifaximin and of Dried Raw Rifaximin

In a three-necked flask equipped with mechanic stirrer, thermometer and reflux condenser, 120 ml of demineralized water, 96 ml of ethyl alcohol, 63.5 g of rifamycin O and 27.2 g of 2-amino-4-methylpyridine are loaded in succession at room temperature. After the loading, the mass is heated at 47±3° C., is kept under stirring at this temperature for 5 hours, then is cooled to 20±3° C. and, during 30 minutes, is added with a mixture, prepared separately, made of 9 ml of demineralized water, 12.6 ml of ethyl alcohol, 1.68 g of ascorbic acid and 9.28 g of aqueous concentrated hydrochloric acid. At the end of the addition, the mass is kept under stirring for 30 minutes at an interior temperature of 20±3° C. and then, at the same temperature, 7.72 g of concentrated hydrochloric acid are dripped until a pH equal to 2.0.

At the end of the addition, the mass is kept under stirring, always at an interior temperature equal to 20° C., for 30 minutes, then the precipitate is filtered and washed by means of a mixture made of 32 ml of demineralized water and of 25 ml of ethyl alcohol. The so obtained "raw rifaximin" (89.2 g) is dried under vacuum at room temperature for 12 hours obtaining 64.4 g of "dried raw rifaximin" which shows a water content equal to 5.6% and a diffractogram corresponding to the polymorphous form β. The product by further drying under vacuum until constant weight gives 62.2 g of dried raw rifaximin having a water content equal to 2.2%, whose diffractogram corresponds to the polymorphous form α.

The product is hygroscopic and the obtained polymorphous form is reversible: the polymorphous form α absorbs water from the atmospheric humidity until to reach, dependent upon the relative humidity and the time of exposure, a water content higher than 4.5% and to turn into the polymorphous form β which in its turn, by drying loses part of the water turning into the polymorphous form α with a water content between 2.0% and 3.0%.

EXAMPLE 2

Preparation of Rifaximin γ

163 Ml of ethyl alcohol and 62.2 g of dried raw rifaximin are loaded at room temperature into a three-necked flask equipped with mechanic stirrer, thermometer and reflux condenser. The suspension is heated at 57±3° C. under stirring until complete dissolution of the solid and at this temperature 70 ml of demineralized water are added in 30 minutes. After the end of the addition the temperature is brought to 30° C. in 40 minutes and is kept at this value until plentiful crystallization, then the temperature is further lowered to 0° C. during 2 hours and kept at this value for 6 hours. The suspension is then filtered and the solid is washed with 180 g of demineralized water.

After drying under vacuum at room temperature until constant weight, 52.7 g of pure rifaximin γ are obtained showing a water content equal to 1.5%.

The form γ is characterized from a powder X-ray diffractogram showing significant peaks at diffraction angles 2θ of 5.0°; 7.1°; 8.4°.

EXAMPLE 3

Preparation of Rifaximin α

62.2 Grams of dried raw rifaximin and 163 ml of ethyl alcohol are loaded at room temperature into a three-necked flask equipped with mechanic stirrer, thermometer and reflux condenser. The suspension is heated at 57±3° C. until complete dissolution of the solid and then 70 ml of demineralized water are added at this temperature during 30 minutes. After the end of the addition the temperature is brought to 30° C. during 40 minutes and is kept at this value until plentiful crystallization. The temperature of the suspension is then brought to about 40° C. and kept at this value during 20 hours under stirring; then the temperature is brought at 0° C. during 30 minutes and the suspension is immediately filtered. The solid is washed with 180 ml of demineralized water and dried under vacuum at room temperature until constant weight obtaining 51.9 g of rifaximin form ox with a water content equal to 2.5% and a powder X-ray diffractogram showing peaks at values of angles 2θ of 6.6°; 7.4°; 7.9°; 8.8°; 10.5°; 11.1°; 11.8°; 12.9°; 17.6°; 18.5°; 19.7°; 21.0°; 21.4°; 22.1°.

EXAMPLE 4

Preparation of Rifaximin α

89.2 Grams of raw rifaximin and 170 ml of ethyl alcohol are loaded at room temperature into a three-necked flask equipped with mechanic stirrer, thermometer and reflux condenser, then the suspension is heated at 57±3° C. until complete dissolution of the solid. The temperature is brought to 50° C. and then 51.7 ml of demineralized water are added at this temperature during 30 minutes. After the end of the addition the temperature is brought to 30° C. in one hour and the suspension is kept for 30 minutes at this temperature obtaining a plentiful crystallization. The temperature of the suspension is brought to 40° C. and kept at this value during 20 hours under stirring and then further lowered to 0° C. during 30 minutes after which the suspension is immediately filtered. The solid is washed with 240 ml of demineralized water and dried under vacuum at 65° C. until constant weight obtaining 46.7 g of rifaximin α with a water content equal to 2.5%.

EXAMPLE 5

Preparation of Rifaximin α

Example 3 is repeated by increasing at 50° C. the temperature at which the suspension is kept and lowering to 7 hours the time in which the suspension is kept at this temperature. The product obtained is equal to that of example 3.

EXAMPLE 6

Preparation of Rifaximin β

The crystallization of the dried raw rifaximin is carried out according to the method described in example 3. The drying under vacuum at room temperature is checked by means of the Karl Fisher method and is stopped when the water content reaches 5.0%: 52.6 g of rifaximin β are obtained characterized from a powder X-ray diffractogram showing peaks at values of angles 2θ of 5.4°; 6.4°; 7.0°; 7.8°; 9.0°; 10.4°; 13.1°; 14.4°; 17.1°; 17.9°; 18.3°; 20.9°.

EXAMPLE 7

Preparation of Rifaximin α Starting from Rifaximin γ

5 Grams of rifaximin γ are suspended in a mixture made of 13 ml of ethyl alcohol and 5.6 ml of water and the suspension is heated at 40° C. during 24 hours under stirring in a 50 ml flask equipped with condenser, thermometer and mechanic stirrer. The suspension is then filtered and the solid is washed with water and then dried under vacuum at room temperature until constant weight. 4 Grams of rifaximin are obtained showing a powder X-ray diffractogram corresponding to that of the polymorphous form α and a water content equal to 2.6%.

EXAMPLE 8

Preparation of Rifaximin γ Starting from Rifaximin α

15 Grams of rifaximin form α and 52.4 ml of ethyl alcohol are loaded into a 250 ml three-necked flask equipped with reflux condenser, thermometer and mechanical stirrer; the suspension is heated under stirring at the temperature of 50° C. until complete dissolution of the solid.

The limpid solution is added with 22.5 ml of water during 30 minutes under stirring, cooled to 30° C. and kept at this temperature during 30 minutes. The formed suspension is cooled to 0° C. under strong stirring and kept at this temperature during 6 hours. A part of the suspension is taken after this period of time, filtered, washed with demineralized water and dried under vacuum at 30° C. until constant weight.

The so obtained product, 3.7 g, shows a diffractogram consistent with that of the form γ and a water content equal to 1.7%.

The remaining part of the suspension is kept at 0° C. for further 18 hours under strong stirring and then is filtered, washed with demineralized water and dried at 30° C. under vacuum until constant weight. 9 Grams of product showing a diffractogram consistent with that of the form γ and a water content equal to 1.6% are obtained.

EXAMPLE 9

Preparation of Rifaximin α Starting from Rifaximin β

5 Grams of rifaximin β having a water content equal to 5.0% are dried under vacuum at +30° C. during 8 hours obtaining 4.85 g of rifaximin α having a water content equal to 2.3%.

EXAMPLE 10

Preparation of Rifaximin β Starting from Rifaximin α

5 Grams of rifaximin α having a water content equal to 2.5% are kept during 40 hours in an atmosphere containing a relative humidity equal to 56% made by means of a saturated aqueous solution of calcium nitrate tetrahydrate. 5.17 Grams of rifaximin β with a water content equal to 5.9% are obtained after this time.

The invention claimed is:

1. A purified rifaximin α, a polymorph of the antibiotic rifaximin, wherein said rifaximin α has a water content of 3% or less, and produces a powder X-ray diffractogram showing peaks at values of the diffraction angles 2θ of 6.6°; 7.4°; 7.9°; 8.8°; 10.5°; 11.1°; 11.8°; 12.9°; 17.6°; 18.5°; 19.7°; 21.0°; 21.4°; 22.1°.

2. The rifaximin α according to claim 1, wherein said water content is between 2.0% and 3.0%.

3. A purified rifaximin β, a polymorph of the antibiotic rifaximin wherein said rifaximin β has a water content higher than 4.5% and produces a powder X-ray diffractogram showing peaks at values of the diffraction angles 2θ of 5.4°; 6.4°; 7.0°; 7.8°; 9.0°; 10.4°; 13.1°, 14.4°; 17.1°; 17.9°; 18.3°; 20.9°.

4. The rifaximin β according to claim 3, wherein said water content is between 5.0% and 6.0%.

5. A purified rifaximin γ, a polymorph of the antibiotic rifaximin wherein said rifaximin γ has a water content between 1.0% and 2.0% and produces a powder X-ray diffractogram showing a mainly amorphous profile and few significant peaks at values of diffraction angles 2θ of 5.0°; 7.1°; 8.4°.

6. A process for the production of rifaximins α, β and γ, comprising:
reacting a molar equivalent of rifamycin O with an excess of 2-amino-4-methylpyridine in a solvent mixture of water and ethyl alcohol in a volumetric ratio between 1:1 and 2:1, for a period of time between 2 and 8 hours, at a temperature between 40° C. and 60° C.,
treating the reaction mass at room temperature with a solution of ascorbic acid in a mixture of water, ethyl alcohol and concentrated aqueous hydrochloric acid,
adjusting the pH of the reaction mass to pH 2.0 with a concentrated aqueous solution of hydrochloric acid,
filtering the suspension,
washing any resulting solid with the water/ethyl alcohol solvent mixture to obtain raw rifaximin,
purifying the raw rifaximin by dissolving it in ethyl alcohol at a temperature between 45° C. and 65° C.,
precipitating the raw rifaximin by adding water and by lowering the temperature of the suspension to between 0° C. to 50° C. under stirring for a period of time between 4 and 36 hours,
filtering the suspension,
washing the resulting solid with water, and
drying it under vacuum or under conditions of normal pressure, with or without a drying agent, at a temperature between room temperature and 105° C., for a period of time between 2 and 72 hours to the water content required to form rifaximin α, β or γ.

7. The process according to claim 6, wherein said 2-amino-4-methylpyridine is from 2.0 to 3.5 molar equivalents.

8. The process according to claim 6, wherein said water added to precipitate the raw rifaximin is in a weight amount between 15% and 70% with respect to the weight amount of ethyl alcohol used for the dissolution.

9. The process according to claim 6 for the production of rifaximin α, wherein after the addition of water to the raw rifaximin, the temperature is lowered to a value between 28° C. and 32° C. in order to cause the beginning of the crystallization,
stirring the resulting suspension at a temperature between 40° C. and 50° C. for a period of time between 6 and 24 hours,
cooling the suspension to 0° C. for a period of time between 15 minutes and one hour,
filtering the suspension, washing the resulting solid with water, and
drying the washed solid until a water content lower than 4.5% is reached.

10. The process according to claim 9, wherein said water content is between 2.0% and 3.0%.

11. The process according to claim 6 for the production of rifaximin β, wherein after the addition of water to the raw rifaximin, the temperature is lowered to a value between 28° C. and 32° C. in order to cause the beginning of the crystallization, stirring the resulting suspension at a temperature between 40° C. and 50° C. for a period of time between 6 and 24 hours, cooling the suspension to 0° C. for a period of time between 15 minutes and one hour, filtering the suspension, washing the resulting solid with water, and drying the washed solid until a water content higher than 4.5% is reached.

12. The process according to claim 11, wherein said water content is between 5.0% and 6.0%.

13. The process according to claim 6 for the production of rifaximin γ, wherein after the addition of water to the raw rifaximin, the temperature is lowered to a value between 28° C. and 32° C. in order to cause the beginning of the crystallization, cooling the suspension to 0° C. for a period of time between 6 and 24 hours, filtering the suspension, washing the resulting solid with water and drying the washed solid until a water content between 1.0% and 2.0% is reached.

14. A process for the production of rifaximin α, comprising suspending rifaximin γ in a solvent mixture of ethyl alcohol/water in a volumetric ratio of 7:3, heating the suspension at a temperature between 38° C. and 50° C., under stirring, for a period of time between 6 and 36 hours, filtering the suspension, washing the resulting solid with water, and drying the washed solid until a water content lower than 4.5% is reached.

15. The process according to claim 14, wherein said water content is between 2.0% and 3.0%.

16. A process for the production of rifaximin β, comprising suspending rifaximin γ in a solvent mixture of ethyl alcohol/water in a volumetric ratio of 7:3, heating the suspension at a temperature between 38° C. and 50° C., under stirring, for a period of time between 6 and 36 hours, filtering the suspension, washing the resulting solid with water, and drying the washed solid until a water content higher than 4.5% is reached.

17. The process according to claim 16, wherein said water content is between 5.0% and 6.0%.

18. A process for the production of rifaximin γ, comprising dissolving rifaximin α or β in ethyl alcohol at a temperature between 50° C. and 60° C., adding demineralized water until an ethyl alcohol/water volumetric ratio equal to 7:3 is reached, cooling the solution to 30° C. under strong stirring, further cooling the resulting suspension to 0° C. for a period of time between 6 and 24 hours, filtering said suspension, washing the resulting solid with water, and drying the solid until a water content lower than 2.0% is reached.

19. A process for the production of rifaximin β, comprising keeping rifaximin α in an ambient environment having a relative humidity higher than 50% for a period of time between 12 and 48 hours until said rifaximin α is converted into rifaximin β.

20. A process for the production of rifaximin α, comprising drying rifaximin β under atmospheric pressure, or under vacuum, or in the presence of a drying agent, at a temperature between the room temperature and 105° C., for a period of time between 2 and 72 hours until said rifaximin β is converted into rifaximin α.

* * * * *